United States Patent
Yang et al.

(10) Patent No.: US 11,701,320 B2
(45) Date of Patent: Jul. 18, 2023

(54) MINERALIZATION AGENT AND MOUTH WASH COMPRISING THE SAME

(71) Applicant: Meiyou (Xi'an) Biotechnology Co., Ltd., Xi'an (CN)

(72) Inventors: Peng Yang, Xi'an (CN); Dong Wang, Xi'an (CN)

(73) Assignee: MEIYOU (XI'AN) BIOTECHNOLOGY CO., LTD., Xi'an (CN)

( * ) Notice: Subject to any disclaimer, the term of this patent is extended or adjusted under 35 U.S.C. 154(b) by 259 days.

(21) Appl. No.: 17/363,055

(22) Filed: Jun. 30, 2021

(65) Prior Publication Data

US 2021/0322292 A1 Oct. 21, 2021

Related U.S. Application Data

(63) Continuation-in-part of application No. PCT/CN2019/124584, filed on Dec. 11, 2019.

(30) Foreign Application Priority Data

Dec. 31, 2018 (CN) .......................... 201811650996.5

(51) Int. Cl.
*A61K 8/64* (2006.01)
*A61K 8/24* (2006.01)
*A61K 8/55* (2006.01)
*A61K 8/66* (2006.01)
*A61Q 11/00* (2006.01)

(52) U.S. Cl.
CPC .................. *A61K 8/64* (2013.01); *A61K 8/24* (2013.01); *A61K 8/55* (2013.01); *A61K 8/66* (2013.01); *A61Q 11/00* (2013.01); *A61K 2800/92* (2013.01)

(58) Field of Classification Search
CPC ... A61K 9/28; A61K 9/50; A61K 8/21; A61K 8/73; A61K 8/66; A61K 8/64; A61K 8/24; A61Q 11/00
USPC ................................... 424/50, 499
IPC .................. A61K 8/736, 8/64, 8/66, 8/69, 8/24, A61K 8/21; A61Q 11/00; A61C 15/041; A46B 11/0003

See application file for complete search history.

(56) References Cited

U.S. PATENT DOCUMENTS

| | | | |
|---|---|---|---|
| 2007/0207212 A1* | 9/2007 | Haynie | A61K 9/5078 424/490 |
| 2014/0186273 A1* | 7/2014 | Moradian-Oldak | A61Q 11/00 424/50 |
| 2016/0199283 A1* | 7/2016 | Hug | A61Q 11/02 132/321 |
| 2019/0380929 A1* | 12/2019 | Sari | A61K 8/64 |

* cited by examiner

*Primary Examiner* — Walter E Webb
(74) *Attorney, Agent, or Firm* — Matthias Scholl P.C.; Matthias Scholl

(57) ABSTRACT

A mineralization agent, including, by weight: 5-50% of a film-forming protein, 5-40% of an amelogenin peptide, 5-30% of a water-soluble phosphate, 4-20% of a tris(2-carboxyethyl) phosphine hydrochloride, and 1-10% of a pH regulator. The film-forming protein is selected from the group consisting of lysozyme, bovine serum protein, insulin, α-lactalbumin, or a mixture thereof.

11 Claims, 6 Drawing Sheets

MINERALIZATION AGENT AND MOUTH WASH COMPRISING THE SAME

CROSS-REFERENCE TO RELAYED APPLICATIONS

This application is a continuation-in-part of International Patent Application No. PCT/CN2019/124584 with an international filing date of Dec. 11, 2019, designating the United States, and further claims foreign priority benefits to Chinese Patent Application No. 201811650996.5 filed Dec. 31, 2018. The contents of all of the aforementioned applications, including any intervening amendments thereto, are incorporated herein by reference. Inquiries from the public to applicants or assignees concerning this document or the related applications should be directed to: Matthias Scholl P. C., Attn.: Dr. Matthias Scholl Esq., 245 First Street, 18th Floor, Cambridge, Mass. 02142.

BACKGROUND

The disclosure relates to a mineralization agent and a mouth wash comprising the same.

The main component of tooth enamel is hydroxyapatite, which is not easy to dissolve under normal oral pH conditions. However, when the glycolysis happens in the oval cavity, the acid produced will act on the teeth, and the outermost enamel surface will be demineralized, thus destroying the regularity of the tooth enamel, and leading to the formation of dental caries. Conventionally, a fluoride is added to a tooth paste to prevent dental caries. However, the fluoride is toxic.

SUMMARY

The disclosure provides a mineralization agent, comprising, by weight: 5-50% of a film-forming protein, 5-40% of an amelogenin peptide, 5-30% of a water-soluble phosphate, 4-20% of a tris(2-carboxyethyl) phosphine hydrochloride, and 1-10% of a pH regulator. The film-forming protein is selected from the group consisting of lysozyme, bovine serum protein, insulin, α-lactalbumin, or a mixture thereof.

In a class of this embodiment, the mineralization agent comprises by weight: 20-40% of the film-forming protein, 20-30% of the amelogenin peptide, 20-30% of the water-soluble phosphate, 10-15% of the tris(2-carboxyethyl) phosphine hydrochloride, and 6-8% of the pH regulator.

In a class of this embodiment, the water-soluble phosphate is disodium hydrogen phosphate, sodium dihydrogen phosphate, or a mixture thereof.

In a class of this embodiment, the pH regulator is sodium carbonate, sodium bicarbonate, potassium carbonate, potassium bicarbonate, dipotassium hydrogen phosphate, dipotassium hydrogen phosphate, sodium benzoate, sodium citrate, or a mixture thereof.

The disclosure also provides a mouth wash, comprising the aforesaid mineralization agent and a HEPES (that is, 4-(2-hydroxyethyl)-1-piperazineethanesulfonic acid) buffer diluted with ultrapure water, and the mass-volume ratio of the mineralization agent to the HEPES buffer is 1 mg: 4-15 mL.

In a class of this embodiment, the mouth wash has a pH ranging from 7 to 7.5.

In a class of this embodiment, the mouth wash further comprises saccharin sodium and sorbose.

In another aspect, the disclosure provides a toothpaste, comprising the aforesaid mineralization agent and an excipient in a mass ratio thereof ranging from 1:2 to 1:5.

In a class of this embodiment, the excipient is selected from the group consisting of a friction agent, moisturizer, thickener, preservative, pigment, essence, or a mixture thereof.

The following advantages are associated with the mineralization agent and the mouth wash comprising the same of the disclosure:

The phase transition of the film-forming protein (lysozyme, bovine serum protein, insulin, α-lactalbumin, and so on) leads to the formation of a two-dimensional protein nanofilm at the gas-liquid and solid-liquid interfaces. The surface of the film has a large number of functional groups, and the potential of the film surface is positive, so that the supersaturated calcium and phosphate ions in saliva can be adsorbed on the film surface through electrostatic force. The amelogenin peptide and phosphate adsorbed on the nanofilm can remineralize the surface of the etched enamel to form a remineralized coating thus preventing the formation of dental caries. The amelogenin peptide controls the orientation of crystalline hydroxyapatite on the surface and induces the generation of a remineralized coating similar to natural enamel.

The nanoparticles generated by the phase transformation reaction between the film-forming protein molecules and tris(2-carboxyethyl) phosphine hydrochloride of the mouth wash are self-assembled to form a protein film with a thickness of about 30-50 nm through the interaction and induction at the acid etched enamel interface. The protein film has small surface roughness, high transparency and good adhesion, and has the same function as fluoride ions to strengthen the remineralization of the enamel surface to generate new hydroxyapatite. The main components of the film are protein and salt, which can effectively prevent the enamel from acid etching and demineralization and prevent the formation of dental caries.

The mineralization agent of the disclosure attaches importance to the remineralization effect of the enamel surface. Because the caries is initially manifested as the demineralization of the enamel surface, the remineralization of the surface can prevent and repair the caries before the teeth is permanently destroyed. After using the mouth wash of the disclosure for a period of time, the surface of the demineralized enamel due to acid corrosion can be remineralized, or the normal teeth can be mineralized, thus preventing the formation of dental caries and inhibiting dentine hypersensitivity. The contact time between mouth wash and teeth is optionally about 30-50 s. The pH of the mouth wash solution remains unchanged after entering the oral cavity. During gargling, a two-dimensional protein nanofilm adsorbing amelogenin peptide and phosphate can be formed on the enamel surface. Thereafter, the tooth surface can be remineralized in saliva.

When the toothpaste of the disclosure is soaked with water, and contacts with the enamel surface, a protein layer for preventing demineralization and inducing remineralization of the enamel surface is formed. In the process of tooth brushing, the protein in the toothpaste will react with tris (2-carboxyethyl) phosphine hydrochloride, resulting in the phase transformation of protein on the enamel surface and the formation of a two-dimensional nanofilm of bio-protein encompassing the amelogenin peptide on the tooth surface.

The main component of the mouth wash and toothpaste comprising the mineralized material of the disclosure are protein, and the water-soluble phosphate and tris(2-carboxyethyl) phosphine hydrochloride are low in content, which causes no harm to human body. The mineralization agent of the disclosure can also be made into other types of products for preventing enamel demineralization.

DETAILED DESCRIPTION

Figure 1:
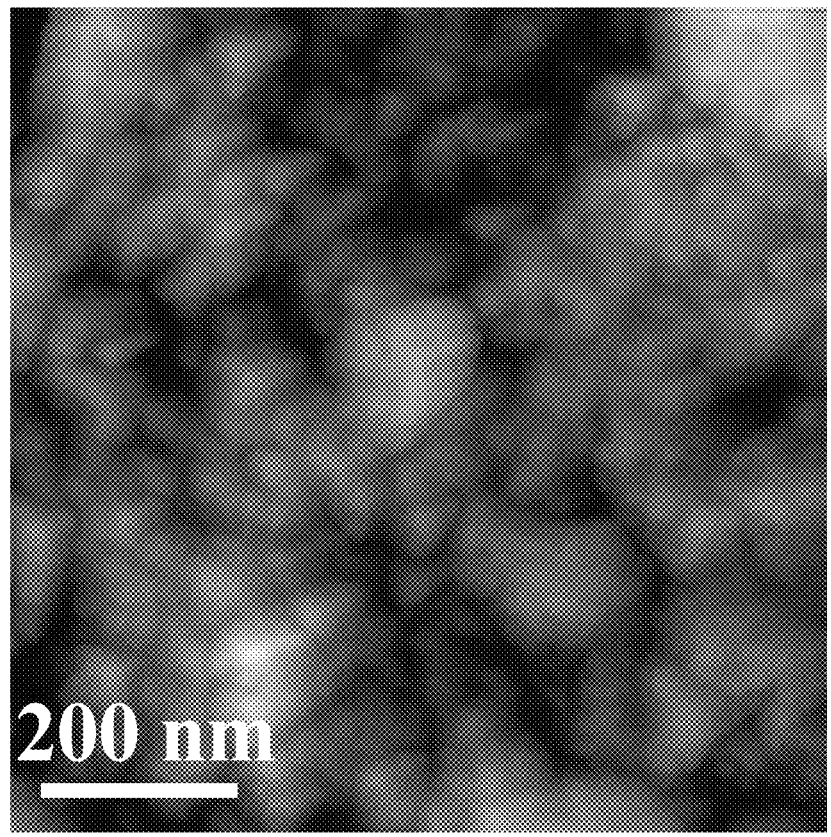
FIG. 1 is an Atomic Force Microscope (AFM) image of a bio-protein two-dimensional nanofilm formed on the surface of a tooth enamel treated by a mouth wash prepared in Example 8 of the disclosure.

To further illustrate, embodiments detailing a mineralization agent and mouth wash comprising the same are described below. It should be noted that the following embodiments are intended to describe and not to limit the disclosure.

Example 1

20 mg of lysozyme, 10 mg of an amelogenin peptide, 10 mg of disodium hydrogen phosphate, 5.2 mg of a tris(2-carboxyethyl) phosphine hydrochloride, and 3.5 mg of sodium bicarbonate were evenly mixed to yield a mineralization agent configured to prevent the demineralization of tooth enamel.

Example 2

100 mg of lysozyme, 50 mg of an amelogenin peptide, 40 mg of disodium hydrogen phosphate, 10.5 mg of a tris(2-carboxyethyl) phosphine hydrochloride, and 4.5 mg of sodium bicarbonate were evenly mixed to yield a mineralization agent configured to prevent the demineralization of tooth enamel.

Example 3

200 mg of lysozyme, 100 mg of an amelogenin peptide, 80 mg of disodium hydrogen phosphate, 18.3 mg of a tris(2-carboxyethyl) phosphine hydrochloride, and 5.1 mg of sodium bicarbonate were evenly mixed to yield a mineralization agent configured to prevent the demineralization of tooth enamel.

Example 4

20 mg of lysozyme, 30 mg of an amelogenin peptide, 30 mg of disodium hydrogen phosphate, 15 mg of a tris(2-carboxyethyl) phosphine hydrochloride, and 5 mg of sodium bicarbonate were evenly mixed to yield a mineralization agent configured to prevent the demineralization of tooth enamel.

Example 5

30 mg of lysozyme, 20 mg of an amelogenin peptide, 20 mg of disodium hydrogen phosphate, 20 mg of a tris(2-carboxyethyl) phosphine hydrochloride, and 10 mg of sodium bicarbonate were evenly mixed to yield a mineralization agent configured to prevent the demineralization of tooth enamel.

Example 6

5 mg of lysozyme, 40 mg of an amelogenin peptide, 30 mg of disodium hydrogen phosphate, 20 mg of a tris(2-carboxyethyl) phosphine hydrochloride, and 5 mg of sodium bicarbonate were evenly mixed to yield a mineralization agent configured to prevent the demineralization of tooth enamel.

Example 7

50 mg of lysozyme, 5 mg of an amelogenin peptide, 15 mg of disodium hydrogen phosphate, 20 mg of a tris(2-carboxyethyl) phosphine hydrochloride, and 10 mg of sodium bicarbonate were evenly mixed to yield a mineralization agent configured to prevent the demineralization of tooth enamel.

Example 8

2 mg of the mineralization agent prepared in Example 1 was added to 10 mL of HEPES (4-(2-hydroxyethyl)-1-piperazineethanesulfonic acid) buffer which had been diluted three times with ultrapure water, to yield a primary mouth wash. When in use, 8 mg of saccharin sodium and 2 mg of sorbose were added to the primary mouth wash and evenly mixed to yield a final mouth wash for preventing the demineralization of tooth enamel.

Example 9

2 mg of the mineralization agent prepared in Example 2 was added to 20 mL of HEPES (4-(2-hydroxyethyl)-1-piperazineethanesulfonic acid) buffer which had been diluted three times with ultrapure water, to yield a primary mouth wash. When in use, 12 mg of saccharin sodium and 4 mg of sorbose were added to the primary mouth wash and evenly mixed to yield a final mouth wash for preventing the demineralization of tooth enamel.

Example 10

2 mg of the mineralization agent prepared in Example 3 was added to 30 mL of HEPES (4-(2-hydroxyethyl)-1-piperazineethanesulfonic acid) buffer which had been diluted three times with ultrapure water, to yield a primary mouth wash. When in use, 14.8 mg of saccharin sodium and 6.3 mg of sorbose were added to the primary mouth wash and evenly mixed to yield a final mouth wash for preventing the demineralization of tooth enamel.

In certain embodiments, lysozyme used in Examples 1-9 was replaced by bovine serum protein, insulin, or α-lactalbumin.

Figure 2:
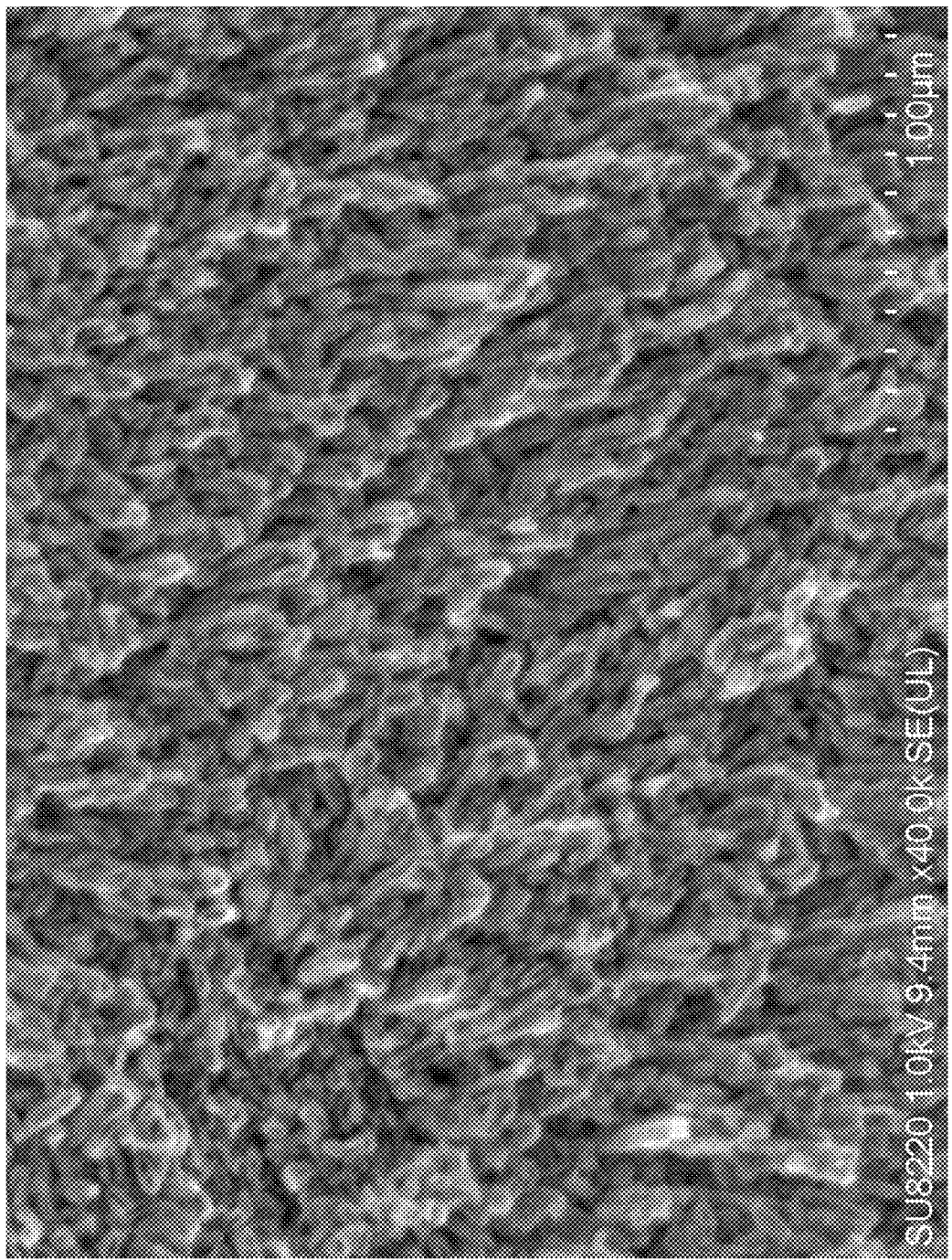
FIG. 2 is a Scanning Electron Microscope (SEM) image of a remineralized coating formed on the surface of a tooth enamel which is first treated by a mouth wash prepared in Example 8 of the disclosure and then mineralized in artificial saliva.
Figure 3:
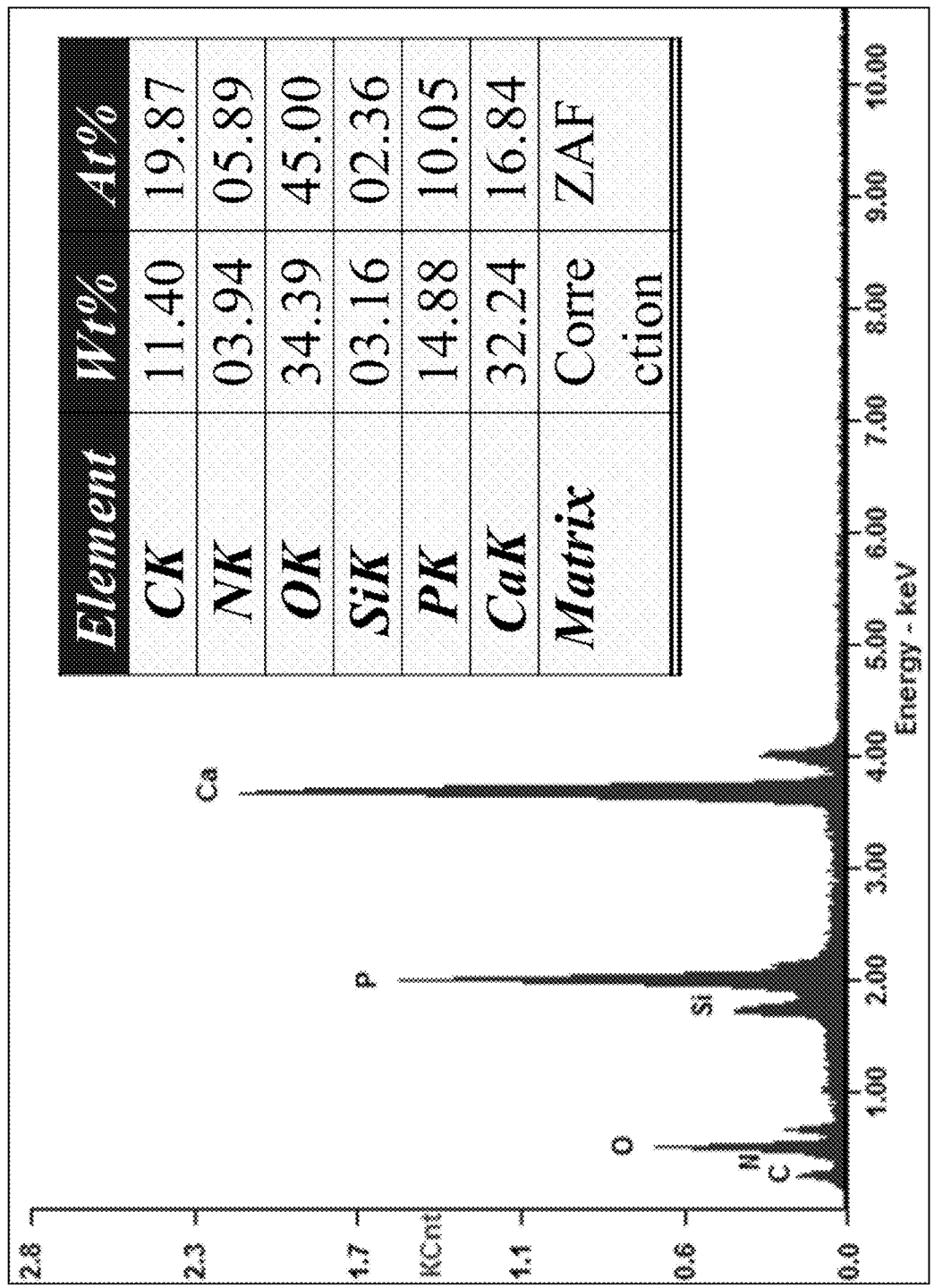
FIG. 3 is an Energy Dispersive X-ray (EDX) spectrum of a remineralized coating formed on the surface of a tooth enamel which is first treated by a mouth wash prepared in Example 8 of the disclosure and then mineralized in artificial saliva.

To illustrate the technical effect of the mouth wash, the performance of the mouth wash obtained in Example 4 was tested as follows:

The tooth enamel was polished, sliced, and etched with acid. The enamel slices were put into the mouth wash, soaked for 1 minute, thereby simulating the process of gargling. As shown in FIG. 1, one minute later, a two-dimensional nanofilm of bio-protein with a thickness of about 30-50 nm was formed on the surface of the tooth enamel. Then, the tooth enamel comprising the nanofilm was put into artificial saliva for biomineralization at 37° C. The artificial saliva was refreshed once a day. In the process of mineralization, the tooth enamel was taken out from artificial saliva every day, washed with ultrapure water, soaked in the mouth wash for 1 min, and then added to artificial saliva again. The process was repeated twice a day. Two weeks later, the surface morphology of the remineralized coating of the tooth enamel was observed by SEM, and the surface of the remineralized coating was scanned by an EDX to analyze the elements of the remineralized coating. The results are shown in FIG. 2 and FIG. 3. The tooth enamel was broken apart, and the cross-section morphology of the remineralized coating of the tooth enamel was observed by SEM. The results are shown in FIG. 4.

Figure 4:
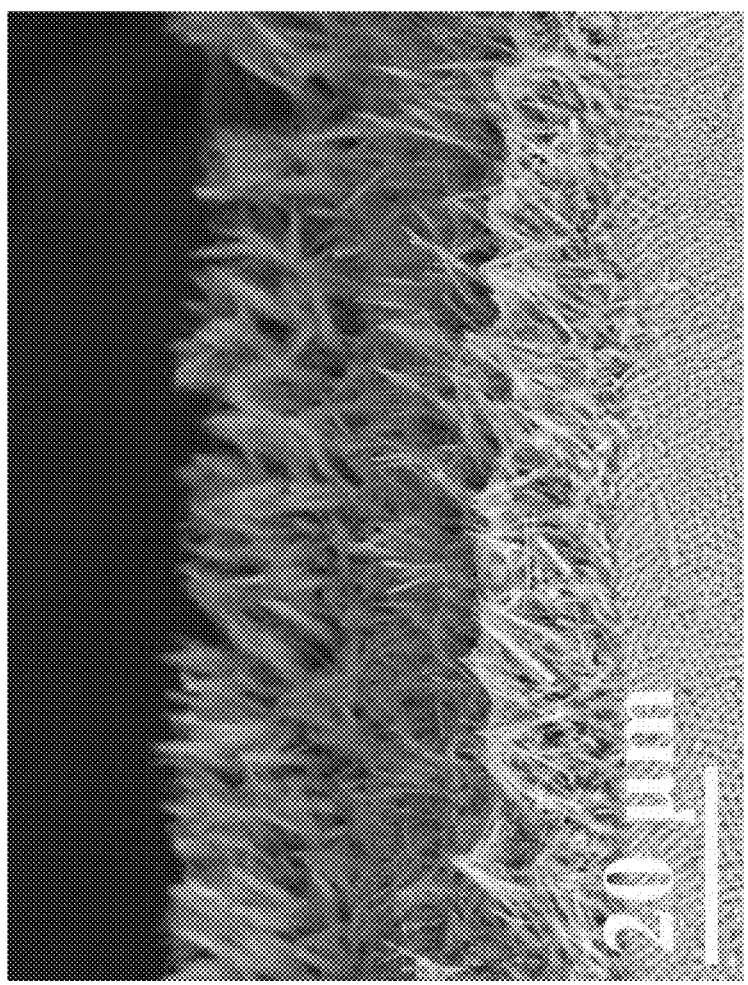
FIG. 4 is a SEM image of cross section of a remineralized coating formed on the surface of a tooth enamel which is first treated by a mouth wash prepared in Example 8 of the disclosure and then mineralized in artificial saliva.

As shown in FIGS. 2-4, the two-dimensional nanofilm of the bio-protein in-situ grew on the tooth enamel. The coated tooth enamel was biomineralized in artificial saliva to form well-oriented hydroxyapatite. The calcium-phosphorus ratio was equal to that of natural tooth enamel. Hydroxyapatite was newly formed on the surface of etched enamel thus preventing demineralization of the enamel and the formation of dental caries.

Figure 5:
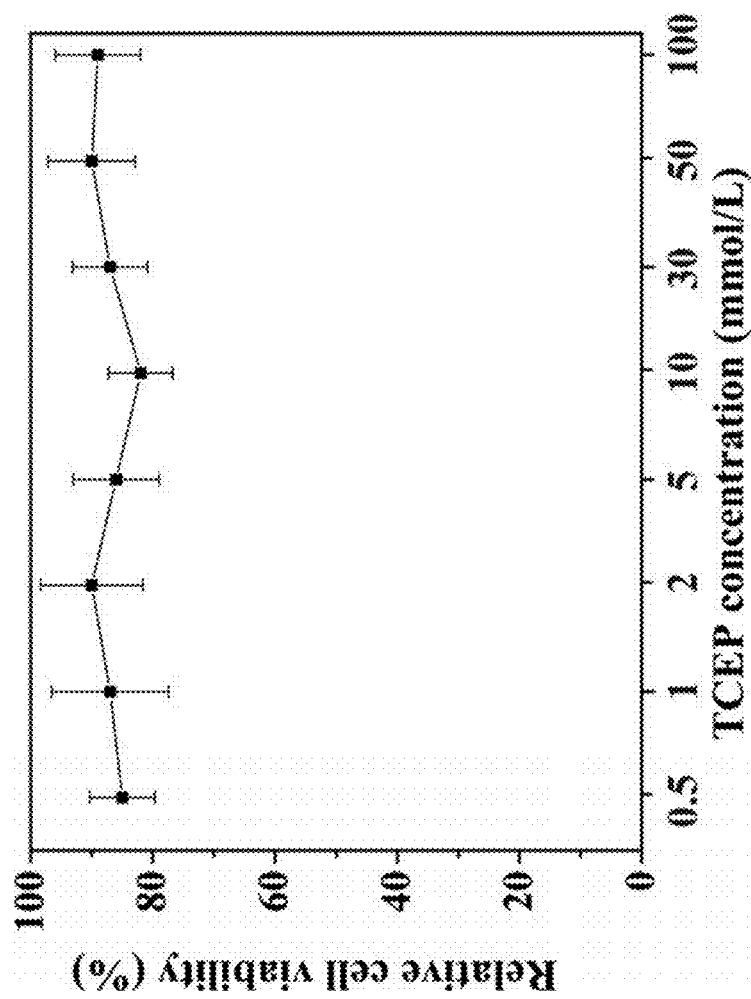
FIG. 5 is a cytotoxic test result of a mouth wash prepared in Example 8 of the disclosure.

The main component of the mouth wash was protein, and the concentration of the tris(2-carboxyethyl) phosphine hydrochloride (TCEP) in the mouth wash was controlled to measure the cytotoxicity of the mouth wash by MTT assay. The absorbance was measured by a microplate reader at 490 nm. The absorbance was proportional to the cell survival rate. The cytotoxicity was determined by the cell survival rate. The higher the cell survival rate, the lower the cytotoxicity. Cell survival rate=$100\% \times ((A)_{test}/(A)_{control}$, $(A)_{test}$ refers to the absorbance of lysozyme (polypeptide) film (i.e. film formed under different concentrations of a tris(2-carboxyethyl) phosphine hydrochloride), and $(A)_{control}$ refers to the absorbance in the absence of lysozyme (polypeptide) film (i.e. film cannot be formed in the absence of a tris(2-carboxyethyl) phosphine hydrochloride). The sample at each concentration was measured three times, and the results were shown in FIG. 5. The results showed that the relative activity of TCEP in the range of 0.5 mmol/L to 100 mmol/L had little change, and the cell activity was maintained above 80% at low or high concentrations, which proved that the cytotoxicity was small.

Figure 6:
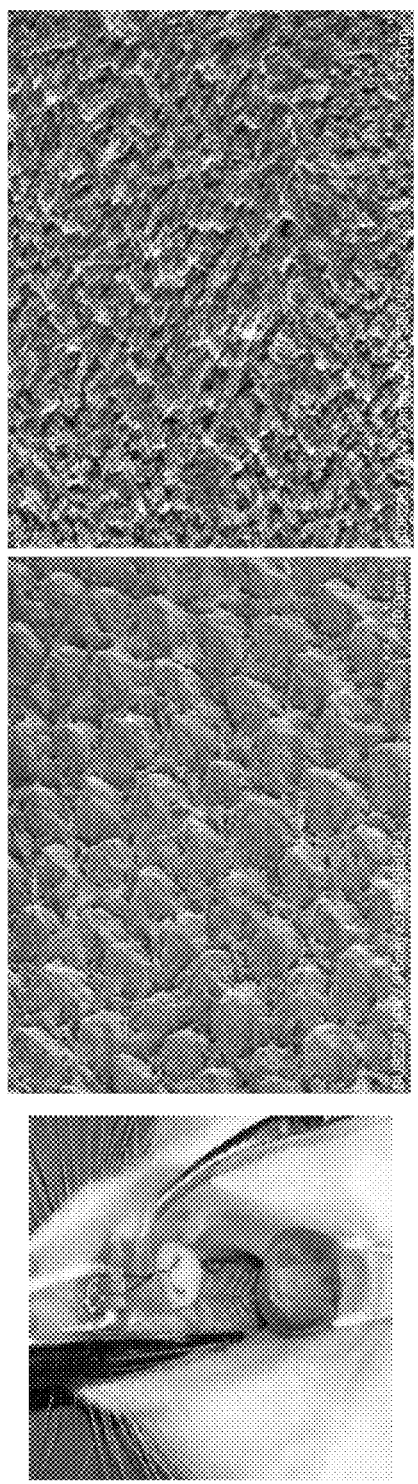
FIG. 6 is a result of animal oral test of a mouth wash prepared in Example 8 of the disclosure.

The tooth enamel comprising the nanofilm was fixed on the teeth of mice, and the coated tooth enamel was biomineralized in the oral cavity of mice. After 30 days, the surface morphology of the tooth enamel was observed. The results were shown in FIG. 6. It can be seen from the figure that the coated tooth enamel fixed on the teeth of mice induces the generation of hydroxyapatite with high orientation in the oral cavity of mice, which proves that the bio-protein film plays a role in mineralization of tooth enamel in vivo and can be applied to the oral environment of human body.

It will be obvious to those skilled in the art that changes and modifications may be made, and therefore, the aim in the appended claims is to cover all such changes and modifications.

What is claimed is:

1. A mineralization agent, comprising, by weight:
   5-50% of a film-forming protein;
   5-40% of an amelogenin peptide;
   5-30% of a water-soluble phosphate;
   4-20% of a tris(2-carboxyethyl) phosphine hydrochloride; and
   1-10% of a pH regulator;
   wherein:
   the film-forming protein is selected from the group consisting of lysozyme, bovine serum protein, insulin, α-lactalbumin, or a mixture thereof.

2. The mineralization agent of claim 1, comprising by weight:
   20-40% of the film-forming protein;
   20-30% of the amelogenin peptide;
   20-30% of the water-soluble phosphate;
   10-15% of the tris(2-carboxyethyl) phosphine hydrochloride; and
   6-8% of the pH regulator.

3. The mineralization agent of claim 1, wherein the water-soluble phosphate is disodium hydrogen phosphate, sodium dihydrogen phosphate, or a mixture thereof.

4. The mineralization agent of claim 2, wherein the water-soluble phosphate is disodium hydrogen phosphate, sodium dihydrogen phosphate, or a mixture thereof.

5. The mineralization agent of claim 1, wherein the pH regulator is sodium carbonate, sodium bicarbonate, potassium carbonate, potassium bicarbonate, dipotassium hydrogen phosphate, dipotassium hydrogen phosphate, sodium benzoate, sodium citrate, or a mixture thereof.

6. The mineralization agent of claim 2, wherein the pH regulator is sodium carbonate, sodium bicarbonate, potassium carbonate, potassium bicarbonate, dipotassium hydrogen phosphate, dipotassium hydrogen phosphate, sodium benzoate, sodium citrate, or a mixture thereof.

7. A mouth wash, comprising a mineralization agent of claim 1 and a HEPES (4-(2-hydroxyethyl)-1-piperazineethanesulfonic acid) buffer diluted with ultrapure water, wherein a mass-volume ratio of the mineralization agent to the HEPES buffer is 1 mg: 4-15 mL.

8. The mouth wash of claim 7, having a pH ranging from 7 to 7.5.

9. The mouth wash of claim 7, further comprising saccharin sodium and sorbose.

10. A toothpaste, comprising a mineralization agent of claim 1 and an excipient in a mass ratio thereof ranging from 1:2 to 1:5.

11. The toothpaste of claim 10, wherein the excipient is selected from the group consisting of a friction agent, a moisturizer, a thickener, a preservative, a pigment, an essence, or a mixture thereof.

* * * * *